(12) United States Patent
Schaller et al.

(10) Patent No.: US 11,580,113 B2
(45) Date of Patent: Feb. 14, 2023

(54) GENERATING PROACTIVE AUDIOVISUAL QUERIES USING VIRTUAL ASSISTANT SOFTWARE APPLICATIONS

(71) Applicant: Optum, Inc., Minnetonka, MN (US)

(72) Inventors: Charles P. Schaller, Minnetonka, MN (US); Mark Gregory Megerian, Rochester, MN (US); Gregory J. Boss, Saginaw, MI (US); Rick A. Hamilton, Charlottesville, VA (US)

(73) Assignee: Optum, Inc., Minnetonka, MN (US)

( * ) Notice: Subject to any disclaimer, the term of this patent is extended or adjusted under 35 U.S.C. 154(b) by 323 days.

(21) Appl. No.: 16/852,938

(22) Filed: Apr. 20, 2020

(65) Prior Publication Data

US 2021/0326344 A1 Oct. 21, 2021

(51) Int. Cl.
| | |
|---|---|
| *G06F 16/2457* | (2019.01) |
| *G06F 16/2453* | (2019.01) |
| *G06F 16/248* | (2019.01) |
| *G06F 16/435* | (2019.01) |
| *G16H 70/40* | (2018.01) |
| *G06F 9/451* | (2018.01) |

(52) U.S. Cl.
CPC ........ *G06F 16/24575* (2019.01); *G06F 9/453* (2018.02); *G06F 16/248* (2019.01); *G06F 16/24549* (2019.01); *G06F 16/24578* (2019.01); *G06F 16/435* (2019.01); *G16H 70/40* (2018.01)

(58) Field of Classification Search
CPC .............. G06F 16/24575; G06F 9/453; G06F 16/24549; G06F 16/24578; G06F 16/248; G06F 16/435; G16H 70/40

USPC ........ 707/706, 719, 722, 723, 748, 769, 805
See application file for complete search history.

(56) References Cited

U.S. PATENT DOCUMENTS 10,825,554 B2 * 11/2020 Zhang ................... G06N 20/00
2010/0198755 A1 8/2010 Soll et al.
(Continued)

OTHER PUBLICATIONS

"Alexa Skills," Amazon.com: WebMD, [article, online], (4 pages). [Retrieved from the Internet Jul. 7, 2020] <URL: https://www.amazon.com/WebMD-Health-Corp/dp/B01MRM361G>.
(Continued)

*Primary Examiner* — Phong H Nguyen
(74) *Attorney, Agent, or Firm* — Alston & Bird LLP

(57) ABSTRACT

Methods and systems for presenting a proactive audiovisual query using a virtual assistant software application. The methods correspond to retrieving user experience data associated with a user profile for the virtual assistant software application, wherein the user experience data define one or more user experience events for the user profile. The methods further include retrieving subject matter domain data associated with the one or more user experience events, wherein the subject matter domain data define one or more probabilistic event effects for the one or more user experience events and determining, based on the user experience data and the subject matter domain data, one or more optimal query items, wherein the one or more optimal query items are associated with at least one of the one or more probabilistic event effects. The methods further include generating the proactive audiovisual query in accordance with the one or more optimal query items.

17 Claims, 11 Drawing Sheets

(56) References Cited

U.S. PATENT DOCUMENTS

| | | | |
|---|---|---|---|
| 2011/0118555 A1* | 5/2011 | Dhumne | A61M 21/02 600/300 |
| 2012/0221349 A1* | 8/2012 | Mora | G16H 50/70 705/2 |
| 2013/0149683 A1 | 6/2013 | Steerman | |
| 2013/0211472 A1* | 8/2013 | Blomqvist | A61N 1/36585 607/18 |
| 2016/0004834 A1 | 1/2016 | Criner | |
| 2017/0337326 A1* | 11/2017 | Zhang | G06F 16/951 |
| 2019/0355472 A1* | 11/2019 | Kutzko | G16H 20/10 |

OTHER PUBLICATIONS

"MyTherapy: Medication Reminder On The App Store," [article, online], (3 pages). [Retrieved from the Internet Jul. 7, 2020] <URL: https://apps.apple.com/us/app/mytherapy-medication-reminder/id662170995>.

"Prescription Drugs," Health Policy Institute, Georgetown University, [article, online], (9 pages). [Retrieved from the Internet Jul. 7, 2020] <URL: https://hpi.georgetown.edu/rxdrugs/>.

Amrita, Parle et al. "Status of Spontaneous Reporting Of Adverse Drug Reaction By Physicians In Delhi," Indian Journal of Pharmacy Practice, vol. 4, Issue 2, Apr.-Jun. 2011, pp. 29-36.

Appiah, Bernard et al. "Factors That Influence The Intention To Use Mobile Phone Caller Tunes For Patient Reporting Of Adverse Drug Reactions: A Qualitative Study," Therapeutic Advances in Drug Safety, vol. 10, (2019), pp. 1-9. DOI: 10.1177/2042098619871190.

Cowie, Julie et al. "ASYMS ©—SERAT: A Side-Effect Risk Assessment Tool To Predict Chemotherapy Related Toxicity In Patients With Cancer Receiving Chemotherapy," In Proceedings of the First International Conference on Health Informatics, (2008), pp. 225-230.

Davoodi, Somayeh et al. "Mobile Phone Based System Opportunities to Home-Based Managing of Chemotherapy Side Effects," Acta Inform Med, vol. 24, No. 3, Apr. 6, 2016, pp. 193-196. DOI: 10.5455/aim.2016.24.193-196.

Fox, Patricia et al. "The eSMART Project: Real-Time Symptom Management In The Irish Oncology Setting," cancerprofessional, Summer 2016, pp. 22-24.

Kearney, Nora et al. "Evaluation Of A Mobile Phone-Based, Advanced Symptom Management System (ASyMS ©) In The Management Of Chemotherapy-Related Toxicity," Support Care Cancer, vol. 17, (2009), pp. 437-444. DOI: 10.1007/x00520-008-0515-0.

Larsen, Mark E. et al. "Chemotherapy Side-Effect Management Using Mobile Phones," 30th Annual International IEEE EMBS Conference, Aug. 20-24, 2008, pp. 5152-5155.

Maguire, Roma et al. "The Development Of A Side Effect Risk Assessment Tool (ASyMS ©-SERAT) For Use In Patients With Breast Cancer Undergoing Adjuvant Chemotherapy," Journal of Research in Nursing, Vo. 14, No. 27, (2009), pp. 27-40. DOI: 10.1177/1744987108099235.

McCann, Lisa et al. "Patients' Perceptions And Experiences Of Using A Mobile Phone-Based Advanced Symptom Management System (ASyMS ©) To Monitor And Manage Chemotherapy Related Toxicity," European Journal of Cancer Care, vol. 18, No. 2, Mar. 2009, pp. 156-164.

Tomlinson, Deborah et al. "Initial Development Of The Symptom Screening in Pediatrics Tool (SSPedi)," Support Care Cancer, Aug. 31, 2013, (5 pages). DOI: 10.1007/s00520-013-1945-x.

Zhou, Hongyi et al. "Comprehensive Prediction Of Drug-Protein Interactions And Side Effects For The Human Proteome," Scientific Reports, vol. 5, No. 11090, Jun. 9, 2015, pp. 1-13. DOI: 10.1038/srep11090.

\* cited by examiner

700

| Side Effect ID 701 | Drug Correlation 702 | Side Effect Severity Score 703 | Side Effect Priority Score 704 |
|---|---|---|---|
| S1 | D1 | 0.5 | 0.2 |
| S2 | D1, D2 | 0.9 | 0.7 |
| S3 | D1, D3 | 0.1 | 0.4 |
| S4 | D1, D2, D3 | 0.5 | 0.8 |

| Query Item ID 801 | Side Effect ID 802 | Temporal Cost 803 | Side Effect Priority Score 704 |
|---|---|---|---|
| Q1 | S1 | 20 seconds | 0.2 |
| Q2 | S2 | 40 seconds | 0.7 |
| Q3 | S3 | 10 seconds | 0.4 |
| Q4 | S4 | 30 seconds | 0.8 |

FIG. 8

| Query Item Combination 901 | Combined Temporal Cost 902 | Combined Priority Score 903 |
|---|---|---|
| Q1 + Q3 | 30 seconds | 0.6 |
| Q4 | 30 seconds | 0.8 |

GENERATING PROACTIVE AUDIOVISUAL QUERIES USING VIRTUAL ASSISTANT SOFTWARE APPLICATIONS

BACKGROUND

Various embodiments of the present invention address technical challenges related to audiovisual query generation. By disclosing techniques for efficient and reliable generation audiovisual queries, various embodiments of the present invention overcome the efficiency and reliability challenges of various existing virtual assistant software applications.

BRIEF SUMMARY

In general, embodiments of the present invention provide methods, apparatus, systems, computing devices, computing entities, and/or the like for proactive audiovisual query generation. Certain embodiments utilize systems, methods, and computer program products that perform proactive audiovisual query generation by utilizing at least one of user experience data, subject matter domain data, query opportunity moments, optimal temporal ranges for queries, and time-eligible query item combinations.

In accordance with one aspect, a method is provided. In one embodiment, the method comprises retrieving user experience data associated with a user profile for a virtual assistant software application, wherein the user experience data define one or more user experience events for the user profile; retrieving subject matter domain data associated with the one or more user experience events, wherein the subject matter domain data define one or more probabilistic event effects for the one or more user experience events; determining, based on the user experience data and the subject matter domain data, one or more optimal query items, wherein the one or more optimal query items are associated with at least one of the one or more probabilistic event effects; generating a proactive audiovisual query in accordance with the one or more optimal query items; detecting a query opportunity moment; and causing the virtual assistant software application to present the proactive audiovisual query during the query opportunity moment.

In accordance with another aspect, a computer program product is provided. The computer program product may comprise at least one computer-readable storage medium having computer-readable program code portions stored therein, the computer-readable program code portions comprising executable portions configured to retrieve user experience data associated with a user profile for a virtual assistant software application, wherein the user experience data define one or more user experience events for the user profile; retrieve subject matter domain data associated with the one or more user experience events, wherein the subject matter domain data define one or more probabilistic event effects for the one or more user experience events; determine, based on the user experience data and the subject matter domain data, one or more optimal query items, wherein the one or more optimal query items are associated with at least one of the one or more probabilistic event effects; generate a proactive audiovisual query in accordance with the one or more optimal query items; detecting a query opportunity moment; and cause the virtual assistant software application to present the proactive audiovisual query during the query opportunity moment.

In accordance with yet another aspect, an apparatus comprising at least one processor and at least one memory including computer program code is provided. In one embodiment, the at least one memory and the computer program code may be configured to, with the processor, cause the apparatus to retrieve user experience data associated with a user profile for a virtual assistant software application, wherein the user experience data define one or more user experience events for the user profile; retrieve subject matter domain data associated with the one or more user experience events, wherein the subject matter domain data define one or more probabilistic event effects for the one or more user experience events; determine, based on the user experience data and the subject matter domain data, one or more optimal query items, wherein the one or more optimal query items are associated with at least one of the one or more probabilistic event effects; generate a proactive audiovisual query in accordance with the one or more optimal query items; detecting a query opportunity moment; and cause the virtual assistant software application to present the proactive audiovisual query during the query opportunity moment.

BRIEF DESCRIPTION OF THE SEVERAL VIEWS OF THE DRAWINGS

Figure 1:
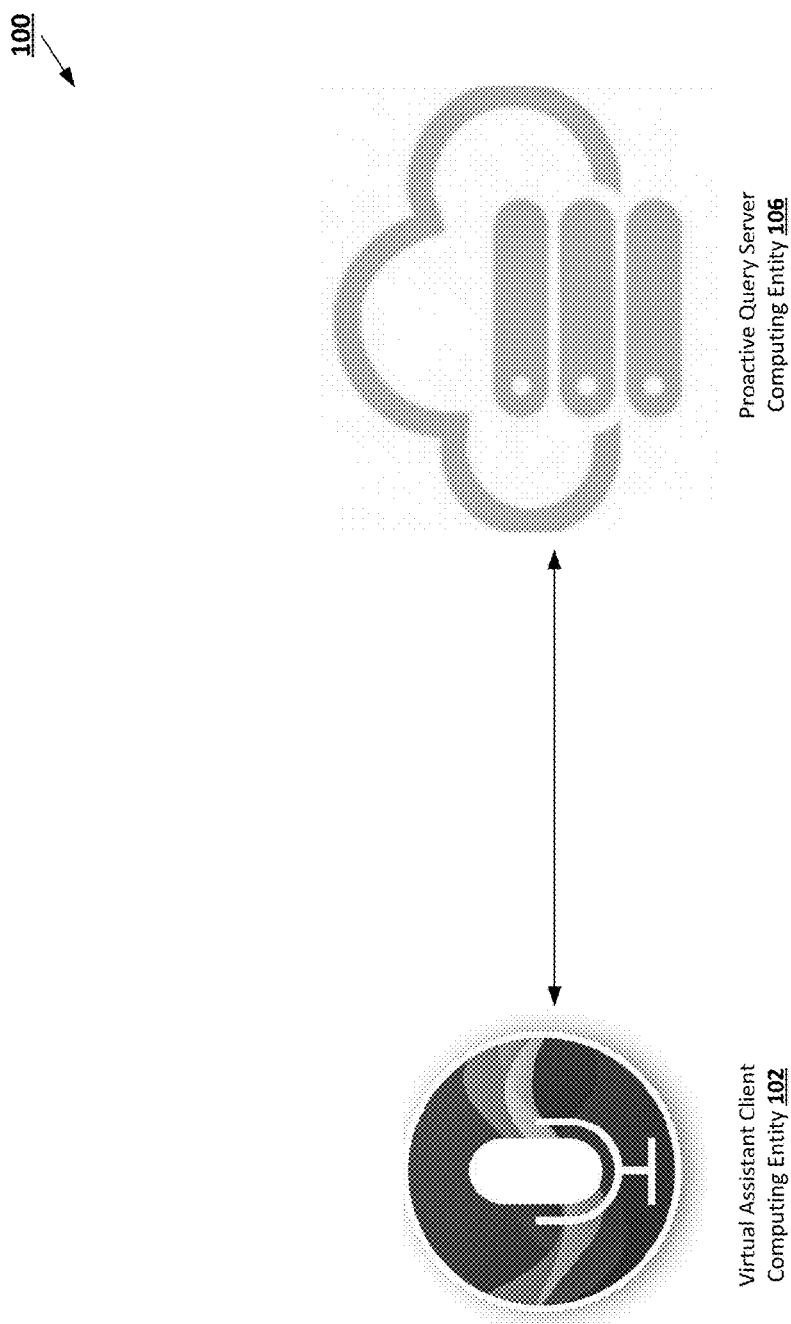
Figure 2:
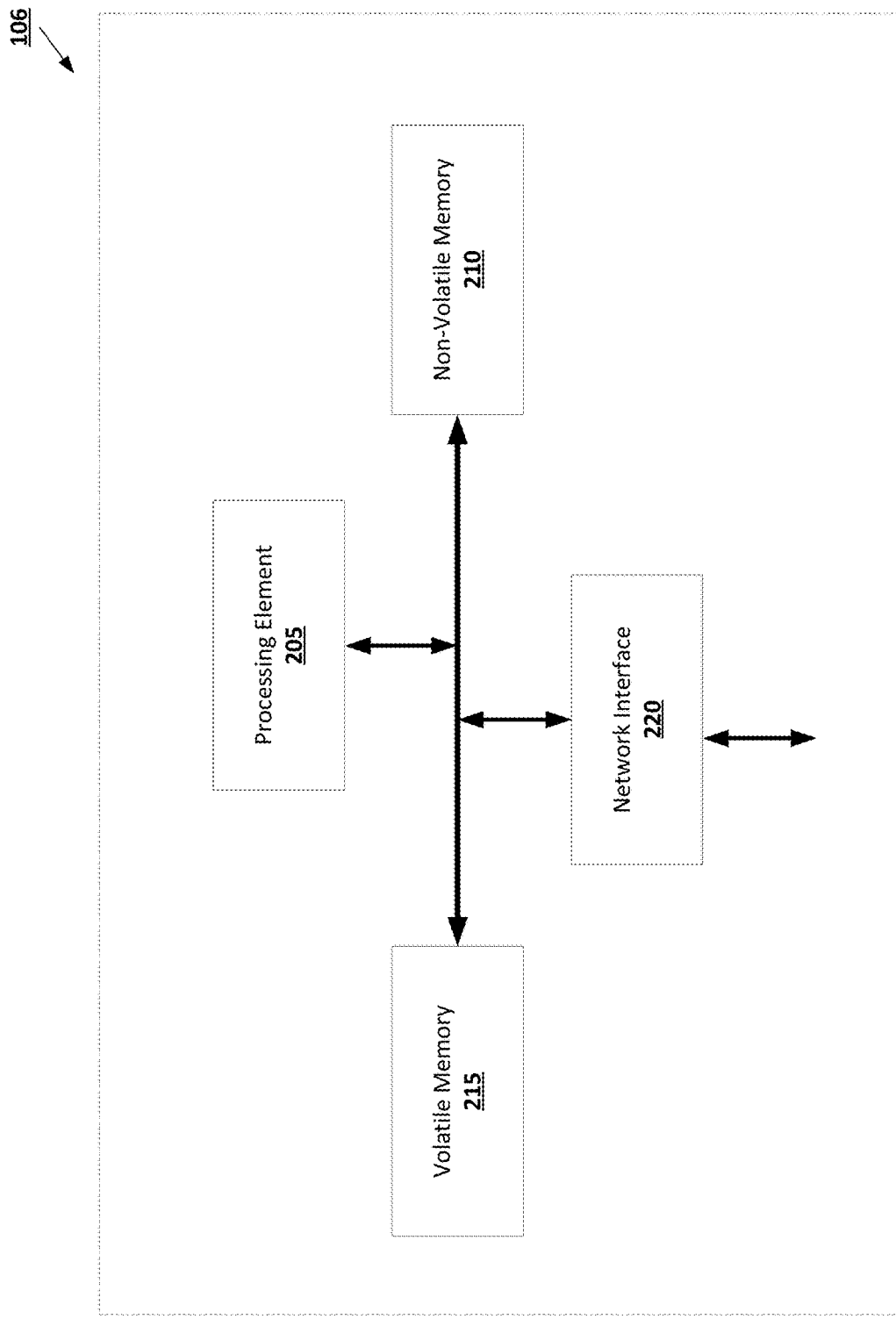
Figure 3:
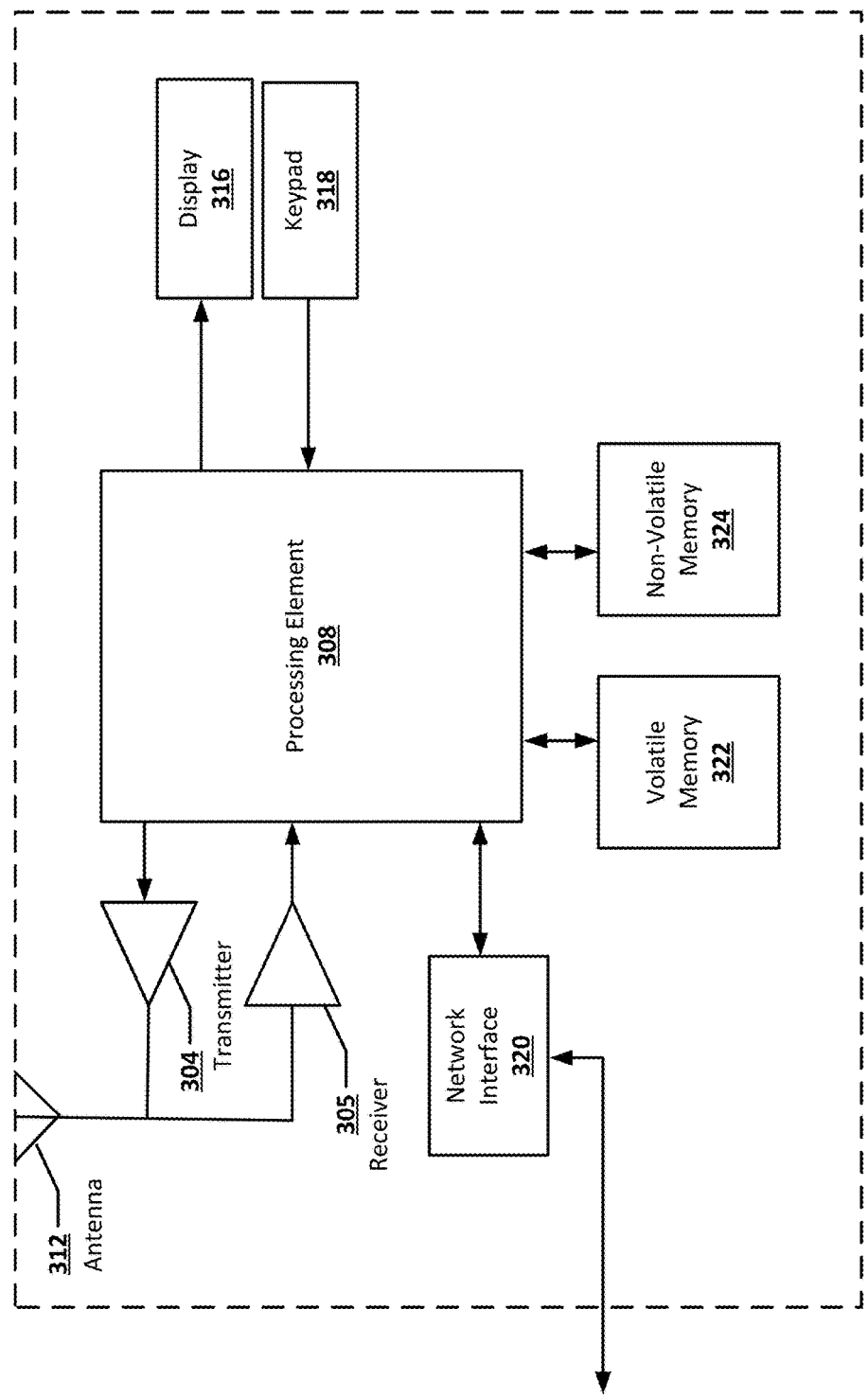
Figure 4:
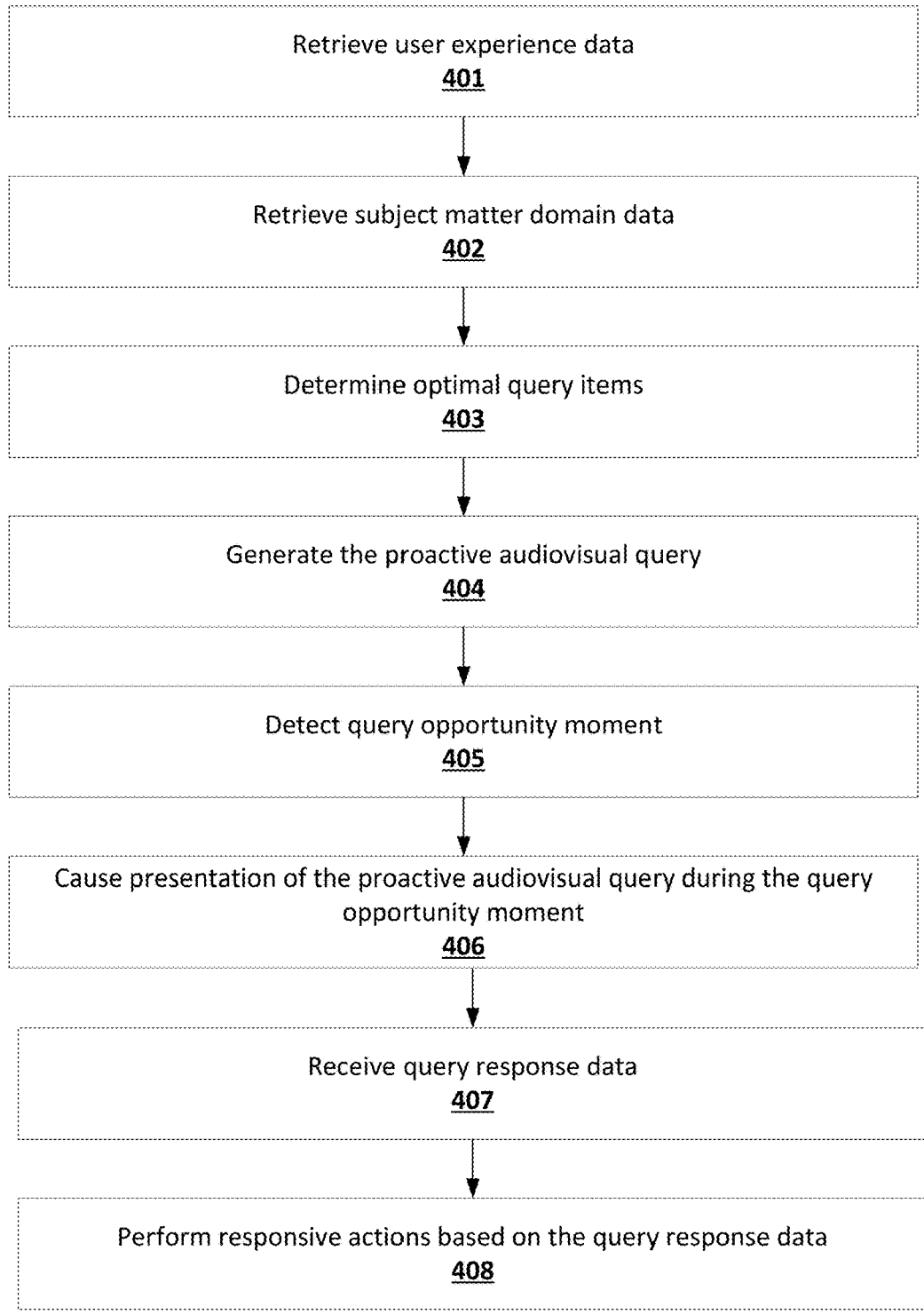
Figure 5:
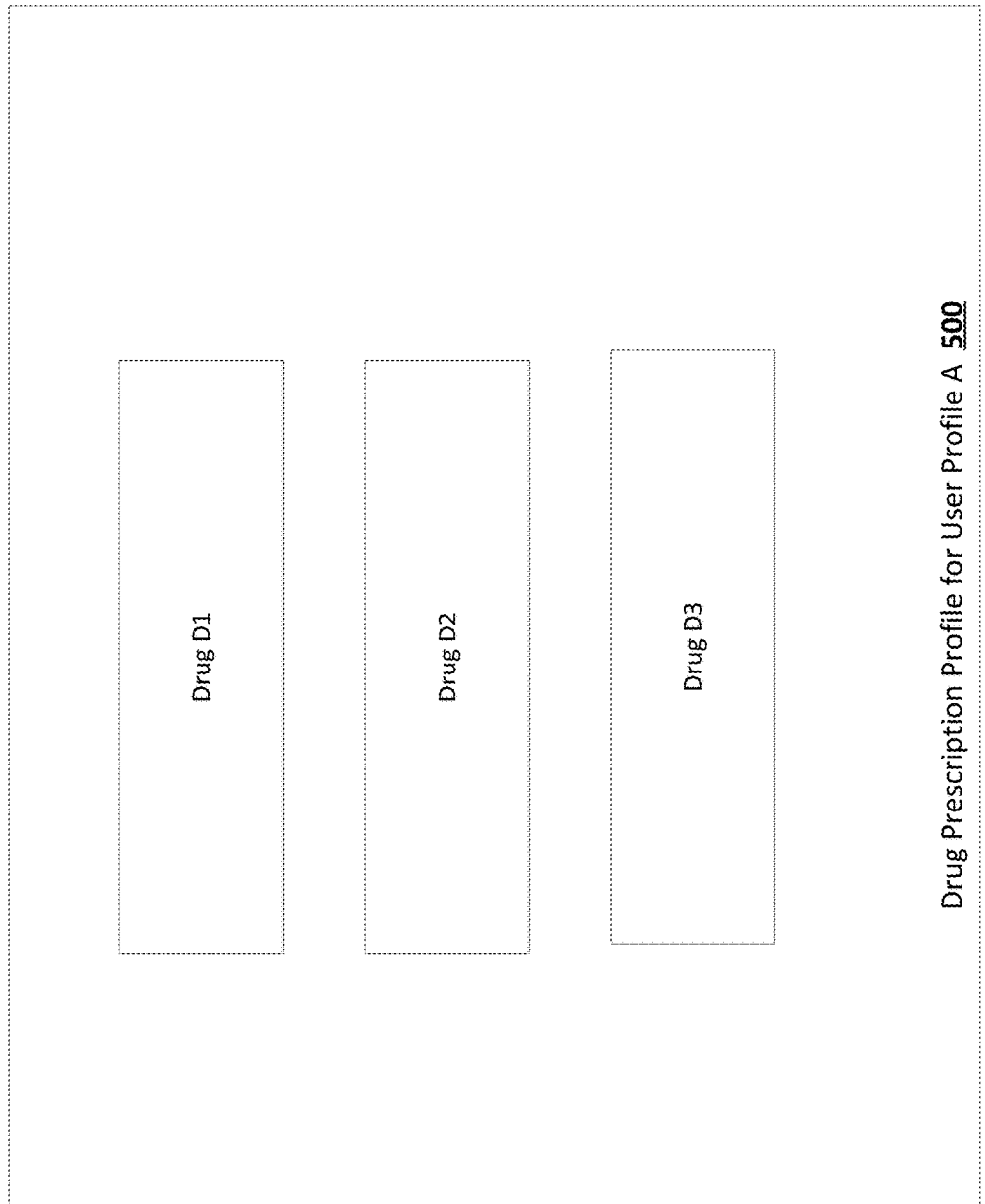
Figure 6:
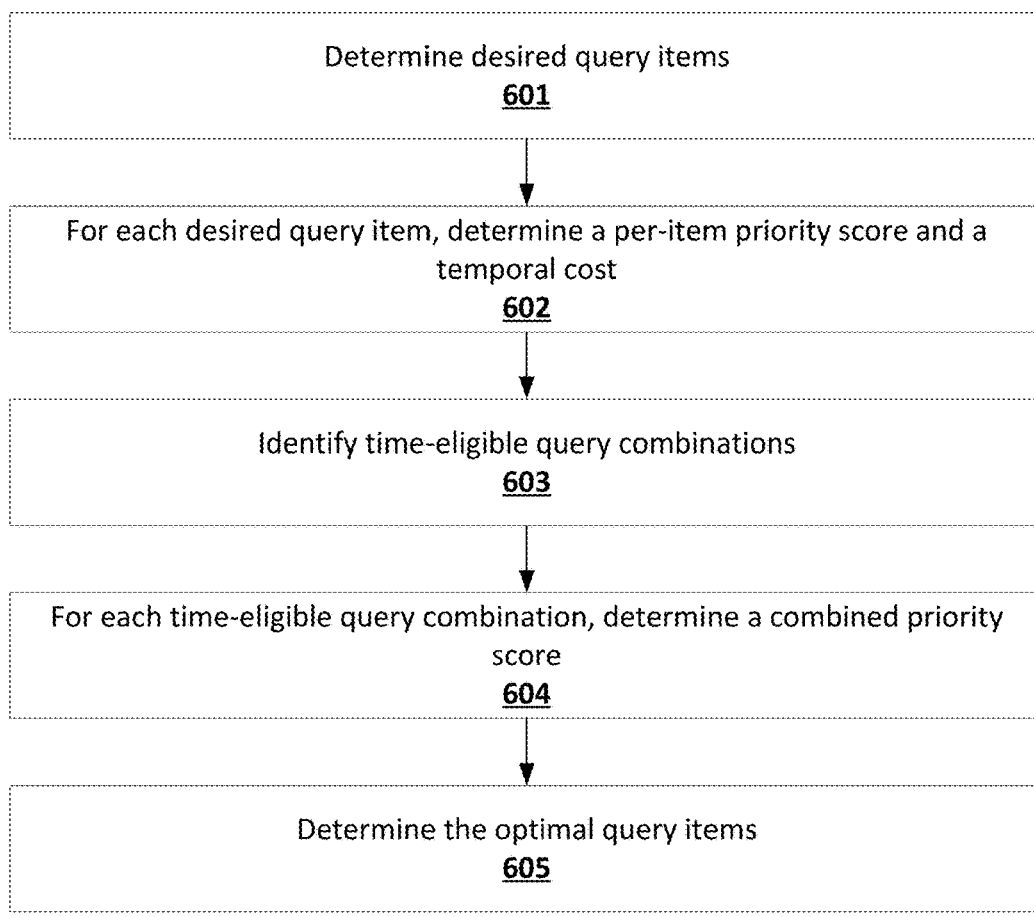
Figure 10A:
Figure 10B:
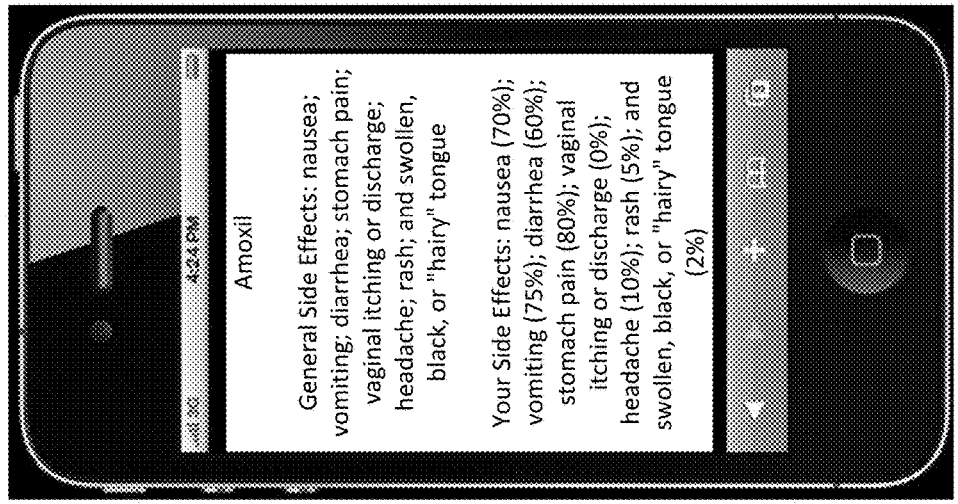

Having thus described the invention in general terms, reference will now be made to the accompanying drawings, which are not necessarily drawn to scale, and wherein:

FIG. 1 is an exemplary overview of a system that can be used to practice embodiments of the present invention;

FIG. 2 illustrates an example server in accordance with some embodiments discussed herein;

FIG. 3 illustrates an example virtual assistant client computing entity in accordance with some embodiments discussed herein;

FIG. 4 illustrates a flow diagram depicting an example of a computer-implemented method for performing responsive actions based on responsive outputs obtained in response to an audiovisual query in accordance with some embodiments discussed herein;

FIG. 5 illustrates a conceptual data model representing a drug prescription profile in accordance with some embodiments discussed herein;

FIG. 6 illustrates a flow diagram depicting an example of a computer-implemented method for determining optimal query items in accordance with some embodiments discussed herein;

FIGS. 7-9 illustrate example output tables generated in response to an example query item computation process in accordance with some embodiments discussed herein; and FIGS. 10A and 10B illustrate example Augmented Reality (AR) views in accordance with some embodiments discussed herein.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

Overview

This invention utilizes a virtual assistant software application that is intelligent, adaptive, and facilitates presentation of a proactive audiovisual query based on user experience data and subject domain data to anticipate and identify side effects of drugs taken by a user. The virtual assistant software may be used as part of a standalone service, application, or device or it may be applied to an existing service application or ambient computing device such as Apple Siri®, Google Home™, Amazon Echo™, etc. The proactive audiovisual query includes a series of drill down questions to gather specific details related to the user's probabilistic drug side effects. In this case, the virtual assistant software application includes computer-implemented methods that can build a knowledge base for drug side effects based on data from a plurality of different in order to detect early potentially adverse drug side effects. Moreover, the virtual assistant application may determine a best time to present the proactive audiovisual query.

Technical Problems

The anxiety about medication adverse effects and illness may cause users to wrongly amplify their perception of benign feelings and physical symptoms. Understanding ahead of time the risks, side effects, and feelings associated with a medication may better inform and prepare users. However, it is difficult to reliably assess a user's reactions to drugs. For example, should open-ended queries or structured queries about specific symptoms be used to obtain relevant information about the user's drug side effects? Also, at what time (e.g., immediately following the user taking the drug, after exercising, after eating, two hours after taking the drug, etc.) should the queries be asked to ensure that the user's symptoms and feelings are related to the drug. For example, asking queries after the side effect has subsided may yield inaccurate information about the presence or severity of the particular side effect. It is also difficult to identify the proper queries to ask a user to obtain information as well as an optimal computer-implemented method by which to ask such questions (e.g., written, audio-only, audio-visual, etc.). Entirely open-ended queries (which may be medication agnostic) are likely insufficient to obtain relevant information from some users.

Additionally, the number of drug side effects can be overwhelmingly large and computationally challenging. Moreover, the large drug data sets do not accommodate and/or address a specific user's medication history including all currently and recently prescribed drugs, previous adverse drug reactions, adherence to a prescribed medicinal treatment regimen and the patient's contextual environment.

Technical Solutions

To solve the foregoing technical problems, an exemplary embodiment of the present invention provides a virtual assistant software application that can retrieve a plurality of user experience data elements associated with a user profile and subject matter domain data (e.g., information concerning the drug taken by the user) in order to generate a proactive audiovisual query. Using subject matter domain data and specific user data, the range of data sets to investigate in order to form queries is reduced, which in turn reduces computational complexity of query generation, as well as storage complexity of input data needed to generate queries. The proactive audiovisual query includes a plurality of questions to obtain clarification and/or additional information about drug use and drug side effects specific and relevant to the user. The proactive audiovisual query may reduce system load (e.g., fewer follow-up questions), provide a faster response, and learn a question style that returns highly confident results. As such, aspects of the disclosure can produce both result oriented and performance-oriented efficiencies.

In an example embodiment, the virtual assistant software application may be embodied as software and delivered as part of an ambient computing device. Once installed on the ambient computing device, the virtual assistant software application may logically and/or physically become part of the ambient computing device and thus the proactive audiovisual query functionality may become part of the virtual assistant functionality. Accordingly, the present invention provides technical advantages by facilitating fast and efficient data mining using refined input. Additionally, embodiments include functionality for generating user queries, presenting queries at a time the user is willing to respond, and obtaining responses to detect early clues about adverse drug effects to potentially notify the user's primary care physician.

Definitions

The term "proactive audiovisual query" refers to an electronically managed data object that describes audiovisual data (i.e., audio data, visual data, or both audio data and visual data) for a request for one or more information entries related to a subject, where the audiovisual data is configured to be presented to a user via a personal assistant software application at a time selected by a computer application. The proactive audiovisual query is used to assess a user's reactions, events, or other performance characteristics with respect to a topic or subject by requesting, from the user, information about the subject. Such requests may be expressed using interrogative sentences, statements or words interpreted as a request for information. In some embodiments, the proactive audiovisual query may be presented to a user in an audio form and/or a visual textual form. In an example context, non-limiting examples of a topic or subject includes medicines or drugs used to treat, prevent, or alleviate symptoms of a disease, as well as side effects of medicines or drugs used to treat, prevent, or alleviate symptoms of a disease.

The term "virtual assistant software application" refers to a software application configured to provide proactive query capabilities to a plurality of virtual assistant devices (e.g., Apple Siri®, Google Home™, Amazon Echo™, etc.). In some embodiments, the virtual assistant software application facilitates the virtual assistant devices to communicate with each other and with a variety of Internet of Things (IoT) devices and/or service devices to collect user data, collect environmental data, and learn from the user data and environmental data. The virtual assistant software application may analyze such data to generate proactive audiovisual queries that are relevant and time specific. The virtual assistant software application may be configured to analyze the data collected from the virtual assistant devices and the variety of other services and devices as well as other relevant data associated with the user (e.g., medical history, daily schedule, known allergies, etc.), and then to utilize the collected data to analyze various timing options in order to select one or more optimal times to present the proactive audiovisual query to the user. Furthermore, the virtual assistant software application may be configured to identify and select an optimal or preferred method by which to ask such queries (e.g., a written method, an audio-only method, an audio-visual method, etc.). The queries or query items selected by the virtual assistant software may be closed or open question types, where closed questions each have a fixed set of possible responses (e.g., multiple choices, yes/no, true/false, rank ordering, scoring, etc.), and open questions allow users to answer in a more free-form manner. The type and method of such query items are determined by the virtual assistant software as likely sufficient to obtain relevant information.

The term "user experience data" refers to an electronically managed data object representing one or more actions performed by a user profile and/or one or more observations related to the user profile. For example, action and observations may be about a user's performance, response to various forms of presented media, actions taken by the user (walking, exercising, working, reading, watching, listening, etc.), or the like. The user experience data may be captured by a virtual assistant software application, one or more client devices (e.g., a client device associated with a medical provider system), and/or one or more IoT devices. In an example context, non-limiting examples of user experience data include but are not limited to drug side effects that have been recorded to have been experienced by a user associated with a user profile. In an example context, non-limiting examples of user experience data include but are not limited to drugs that have been recorded to have been consumed by the user associated with a user profile.

The term "user experience event" refers to an electronically managed data object comprising data described by the user experience data. For example, user experience events include actions performed by a user or observations related to a user (e.g., user is taking Drug A at 9:00 am). In an example context, non-limiting examples of user experience event include but are not limited to one or more drug use events and one or more drug assignment events. Drug use events describe any actions and observations related to, for example, drug side effects such as a date and time a drug side effect was received by the virtual assistant software application, and characteristics of the drug side effect. Drug assignment events describe any actions and observations related to, for example, a date and time the user consumes a drug, does not consume a drug, or is assigned a drug by a medical professional.

The term "user profile" refers to an electronically managed data object representing a collection of attributes specific to a user and/or a user's specific medical data. The user profile may include various information such as, but not limited to, medical history, current and past medications and allergies, immunizations, vital signs, personal statistics such as age and weight, and the like.

The term "subject matter domain data" refers to a collection of one or more electronically managed data objects that describe one or more probabilistic event effects for one or more potential user experience events. For example, given a user experience event of taking Drug A, the probabilistic event effects may include one or more potential side effects of taking the Drug A. In an example context, EMRs (electronic medical records), EHRs (electronic health records), health measurement systems such as the Patient Reported Outcomes for Common Terminology Criteria for Adverse Events (PRO-CTCAE), the United States Food and Drug Administration (FDA) drug labels, Common Terminology Criteria for Adverse Events (CTCAE), and/or medical knowledge bases are mined or searched for associated terms or derivatives of the user experience event for side effects, diseases, or relevant information. Data from these health records and medical knowledge bases may include treatment data, patient history, demographic information, disease information, symptoms, age, genetics, other indicators of likelihood related to a particular abnormality, drug side effect, or disease, and/or other medical findings which enrich the determination of probabilistic event effects. For example, whether a user is female, has a history of high blood pressure, and is taking a birth control drug may indicate a likelihood of having probabilistic event effects such as headache, nausea, amenorrhea, and/or increased cardiovascular risks. In this case, the user's probabilistic event effects is determined if the one or more user experience events includes the terms, a threshold number of the terms, or particular combinations of terms from the patient's medical records and/or medical knowledge base. A plurality of terms is identified and the subject domain data is generated and/or enriched from the terms. The probabilistic event effects is inferred as a function of the matched terms and corresponding probabilities of the terms indicating the existence of probabilistic event effects. For diagnosis of the probabilistic event effects, a probabilistic data model is built from the terms and/or relationship information.

The term "probabilistic event effect" refers to an electronically managed data object that describes a probability of an event effect occurring and the magnitude of the consequences related to the event occurring for a user. For example, such event effects may be about a user's reactions or side effects to medications, or the like. In an example context, non-limiting examples of probabilistic event effect include but are not limited to a probabilistic drug side effect which represents data that describes the probability of the user to develop drug side effect due to his or her user profile, data from health records and medical knowledge bases, and/or subject domain data. The occurrence of the probabilistic event effect is determined from one or more potential user experience events of a user. Subject domain data is used to predict the occurrence of the probabilistic event effect. The probabilistic event effect is determined using a probabilistic data model and is based on adverse event effect data of other users. Using machine-learning and/or other modeling, historical information for other users is used to map input terms associated with the one or more potential user experience events of a user to an output probabilistic event effect. The probabilistic data model indicates variables used to predict probabilistic event effects where variables with the strongest or sufficient correlation or causal relationship to the occurrence of the adverse event effect data are selected and variables with little or no correlation or causal relationship are not selected.

The term "optimal query item" refers to an electronically managed data object that is selected to be provided as part of a proactive audiovisual query to the user during a query opportunity moment. The optimal query item is one or more terms or keywords (e.g., drug brand name, drug generic name, etc.) related to a specific drug. An optimal query item is an item selected from a plurality of potential query items that is to be included in a query or question. In some embodiments, an optimal query item is selected based on a combination of potential query items whose combined temporal cost falls below an optimal temporal range for a proactive audiovisual query during the query opportunity moment and whose combined priority score is higher than the combined priority score for other combinations of potential query items. For example, the user is prescribed a specific thiazide diuretic called hygroton used to treat high blood pressure. Example potential query items may include "thiazide diuretic", "chlorthalidone", and "hygroton." The query item selected as the optimal query item may be hygroton because its priority score is higher (e.g., more relevant to the user because the user is taking the specific brand name drug) than the generic thiazide diuretic chlorthalidone.

The term "query opportunity moment" refers to an electronically managed data object representing a period of time that has been determined to be suitable for providing the proactive audiovisual query. In some embodiments, the query opportunity moment is determined based on whether the user is located proximal to the virtual assistant device and hence if the user is located in close proximity to the virtual assistant device, the proactive audiovisual query can be initiated. In other embodiments, the query opportunity moment is determined based on an optimal temporal range or a combination of the user proximity indicator and the optimal temporal range.

The term "optimal temporal range" refers to an electronically managed data object representing an optimal period of time that is deemed suitable for presenting the proactive audiovisual query. In some embodiments, the optimal temporal range is a period of time preceding and following a user experience event as determined based on daily activities of the user. For example, ten minutes before the user begins an at-home yoga session and ten minutes after the at-home yoga session.

The term "recorded activity pattern" refers to an electronically managed data object representing a user's usual patterns of behavior in daily life, such as, for example, waking up at 6:00 am, running on the treadmill at 6:30 am, listening to the news while eating breakfast at 7:15 am, and so on. In some embodiments, when recording the user's activity pattern, the virtual assistant software application accesses the user's calendar schedule from a calendar service on a client device. In another embodiment, the virtual assistant software application accesses information on the current state of one or more client devices, Internet of Things (IoT) devices, and/or service devices. For example, the virtual assistant software application may request information from the devices to determine the last known state or usage of each device, which is then used to determine and record the user's activity pattern. The device state or usage information is analyzed by the virtual assistant software application to predict user activities and behavior on the basis of each device's usage/state, the time of day, and day of week. The user's willingness to receive and engage with a proactive audiovisual query may depend upon the recorded activity pattern of the user. For example, the user may perceive an incoming query after listening to the news while eating breakfast acceptable whereas the user may find the incoming query unacceptable when practicing yoga.

The term "estimated time capacity" refers to an electronically managed data object representing an amount of time that is available for providing a proactive audiovisual query during an optimal temporal range. For example, the optimal temporal range of two minutes after the user eats breakfast (e.g., 7:15 am to 7:17 am) is associated with a two-minute estimated time capacity.

The term "per-item priority score" refers to an electronically managed data object representing an estimated significance of a corresponding query item to conditions of a corresponding user profile. For example, the per-item priority score may describe the estimated significance of a drug-side-effect-related query item to a condition of a user profile.

The term "temporal cost" refers to an electronically managed data object representing an estimated amount of time for presenting a query item and receiving a response to the query item from the user. For example, the temporal cost may be calculated based on the lexical semantic structure of the query item, query type (e.g., open vs closed), query method (e.g., written, audio-only, audio-visual, etc.), historical query-and-answer data, and/or user profile data (e.g., demographic data including health data, age, sex, etc.).

The term "time-eligible query combination" refers to electronically managed data object representing a combination of query items whose combined temporal cost is within the estimated time capacity of a particular optimal temporal range. For example, the time-eligible query combination of query items Q1 and Q2 may be included in a proactive audiovisual query because it meets the estimated time capacity of two minutes.

The term "user proximity indicator" refers to a value indicating whether the user is estimated to be close to a specified location within a physical environment of a virtual assistant device. A proximity sensor of the virtual assistant device detects a proximity of the user to the virtual assistant device. Once detected, the proximity sensor generates an indication of user proximity to the virtual assistant software application, thereby providing the virtual assistant software application with awareness of the user and enabling the virtual assistant software application to present the proactive audiovisual query. In some embodiments, the proximity sensor comprises one or more of: a radio frequency (RF) sensor, an infrared (IR) sensor, an acoustic sensor, or a Light Detection and Ranging (LiDAR) sensor, and wherein detecting that the user is within a threshold distance of the virtual assistant device comprises tracking a proximity of the user based on a RF signal, an IR signal, an acoustic signal, or a laser light signal of the proximity sensor.

The term "environmental data" refers to electronically managed data object representing data obtained by one or more sensors that describe properties of a physical environment associated with the virtual assistant device. Environmental data may include temperature data, pollen count, humidity, noise level, light level, and other information that may impact the user's ability to provide a response to the proactive audiovisual query. In some embodiments, the environmental data is obtained by accessing a lighting system connected to the virtual assistant device, or devices connected to the virtual assistant device such as appliances or home automation devices, IoT devices, etc.

Computer Program Products,
Computer-Implemented Methods, and Computing Entities

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magneto resistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as computer-implemented methods, apparatus, systems, computing entities, computing entities, and/or the like. As such, embodiments of the present invention may take the form of an apparatus, system, computing entity, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing entities, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically configured machines performing the steps or operations specified in the block diagrams and flowchart illustrations. Accordingly, the block diagrams and flowchart illustrations support various combinations of embodiments for performing the specified instructions, operations, or steps.

Exemplary System Architecture

FIG. 1 provides an illustration of an exemplary embodiment of the present invention. FIG. 1 shows a system 100 including an example network architecture for the system 100, which may include one or more devices and subsystems that are configured to implement some embodiments discussed herein. As shown in FIG. 1, the system 100 may comprise the virtual assistant client computing entity 102, a network, the proactive query server computing entity 106, and/or the like. Each of the components of the system 100 may be in electronic communication with, for example, one another over the same or different wireless or wired networks as discussed herein.

In the example illustrated embodiment of FIG. 1, the system 100 may include the proactive query server computing entity 106 and a plurality of user profiles, which can be embodied as a part of, for example, the proactive query server computing entity 106 of FIG. 2 and/or database, among other devices (not shown). In some embodiments, the proactive query server computing entity 106 may generate proactive audiovisual queries and user profiles. The generated proactive audiovisual queries and user profiles are stored via one or more data repositories which may be stored as a part of and/or in communication with one or more virtual assistant client computing entities 102. The one or more data repositories may further include a subject matter domain data accessed and stored by the proactive query server computing entity 106 to facilitate the operations of the system 100.

The virtual assistant client computing entity 102 can communicate with the proactive query server computing entity 106 via a network, and the virtual assistant client computing entity 102 may communicate with one another and/or other computing entities via the network. In this regard, the network may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, etc.). For example, the network may include a cellular telephone, an 802.11, 802.16, 802.20, and/or WiMax network. Further, the network may include a public network, such as the Internet, a private network, such as an intranet, or combinations thereof, and may utilize a variety of networking protocols now available or later developed including, but not limited to TCP/IP based networking protocols. For instance, the networking protocol may be customized to suit the needs of the group-based communication interface. In some embodiments, the protocol is a custom protocol of JavaScript Object Notation (JSON) objects sent via a Websocket channel. In some embodiments, the protocol is JSON over RPC, JSON over REST/HTTP, and the like.

Virtual assistant client computing entity 102, and/or the proactive query server computing entity 106 may each be implemented as one or more computers, computing entities, desktop computers, mobile phones, tablets, phablets, notebooks, laptops, distributed systems, gaming consoles (e.g., Xbox, Play Station, Wii), watches, glasses, iBeacons, proximity beacons, key fobs, radio frequency identification (RFID) tags, ear pieces, scanners, televisions, dongles, cameras, wristbands, wearable items/devices, items/devices, vehicles, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Any number of virtual assistant client computing entities 102 may be included in the system 100 for accessing and/or implementing aspects of the system 100 discussed herein (e.g., via one or more interfaces). In one embodiment, the proactive query server computing entity 106 may be configured to cause a virtual assistant software application to present a proactive audiovisual query during a query opportunity moment.

The virtual assistant client computing entities 102 may execute an "app" such as the virtual assistant software application to interact with the proactive query server computing entity 106. Such apps are typically designed to execute on mobile devices, such as tablets or smartphones and virtual assistant devices. For example, an app may be provided that executes on mobile device operating systems such as iOS®, Android®, or Windows®. These platforms typically provide frameworks that allow apps to communicate with one another and with particular hardware and software components of mobile devices. For example, the mobile operating systems named above each provide frameworks for interacting with location services circuitry, wired and wireless network interfaces, user contacts, and other applications. Communication with hardware and software modules executing outside of the app is typically provided via application programming interfaces (APIs) provided by the mobile device operating system.

In some embodiments, a display device (which in certain embodiments may be part of one or more virtual assistant client computing entities 102) may project augmented reality (AR) content onto a surface or display for users to view. For example, a mobile device that displays an AR-based drug side effect informational content on a medication bottle or packaging.

Exemplary Proactive Query Server Computing Entity

FIG. 2 provides a schematic of circuitry, some or all of which may be included in, for example, the proactive query server computing entity 106 and/or the virtual assistant client computing entities 102. Any of the aforementioned systems or devices may include the proactive query server computing entity 106 and may be configured to, either independently or jointly with other devices in a network perform the functions of the proactive query server computing entity 106 described herein. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As illustrated in FIG. 2, in accordance with some example embodiments, the proactive query server computing entity 106 or instrument positioning mapping module or circuitry can include various means, such as processing element 205, volatile memory 215, non-volatile memory 210, and/or network interface 220. As referred to herein, "circuitry" includes hardware, software and/or firmware configured to perform one or more particular functions. In this regard, the means of the proactive query server computing entity 106 as described herein may be embodied as, for example, circuitry, hardware elements (e.g., a suitably programmed processor, combinational logic circuit, and/or the like), a computer program product comprising computer-readable program instructions stored on a non-transitory computer-readable medium (e.g., non-volatile memory 210) that is executable by a suitably configured processing device (e.g., processing element 205), or some combination thereof.

As indicated, in one embodiment, the proactive query server computing entity 106 may also include one or more network interfaces 220 for communicating with various computing entities, such as by communicating data, content, information, and/or similar terms used herein interchangeably that can be transmitted, received, operated on, processed, displayed, stored, and/or the like. For instance, the proactive query server computing entity 106 may communicate with other computing entities, one or more virtual assistant client computing entities 102, and/or the like.

As shown in FIG. 2, in one embodiment, the proactive query server computing entity 106 may include or be in communication with one or more processing elements 205 (also referred to as processors, processing circuitry, and/or similar terms used herein interchangeably) that communicate with other elements within the proactive query server computing entity 106 via a bus, for example, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, another circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the proactive query server computing entity 106 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or non-volatile memory 210 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to refer to a structured or unstructured collection of information/data that is stored in a computer-readable storage medium.

Non-volatile memory 210 may also be embodied as a data storage device or devices, as a separate database server or servers, or as a combination of data storage devices and separate database servers. Further, in some embodiments, non-volatile memory 210 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third-party provider and where some or all of the information/data required for the operation of the relevancy prediction system may be stored. As a person of ordinary skill in the art would recognize, the information/data required for the operation of the relevancy prediction system may also be partially stored in the cloud data storage system and partially stored in a locally maintained data storage system.

Non-volatile memory 210 may include information/data accessed and stored by the proactive query server computing entity 106 to facilitate the operations of the system. More specifically, non-volatile memory 210 may encompass one or more data stores configured to store information/data usable in certain embodiments.

Exemplary Virtual Assistant Client Computing Entity

FIG. 3 provides an illustrative schematic representative of the virtual assistant client computing entity 102 that can be used in conjunction with embodiments of the present invention. As shown in FIG. 3, the virtual assistant client computing entity 102 can include an antenna 312, a transmitter 304 (e.g., radio), a receiver 305 (e.g., radio), and a processing element 308 that provides signals to and receives signals from the transmitter 304 and receiver 305, respectively. The signals provided to and received from the transmitter 304 and the receiver 305, respectively, may include signaling information/data in accordance with an air interface standard of applicable wireless systems to communicate with various entities, such as the proactive query server computing entity 106, another virtual assistant client computing entity 102, and/or the like. In this regard, the virtual assistant client computing entity 102 may be capable of operating with one or more air interface standards, communication protocols, modulation types, and access types. More particularly, the virtual assistant client computing entity 102 may operate in accordance with any of a number of wireless communication standards and protocols. In a particular embodiment, the virtual assistant client computing entity 102 may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, wireless universal serial bus (USB) protocols, and/or any other wireless protocol.

Via these communication standards and protocols, the virtual assistant client computing entity 102 can communicate with various other entities using concepts such as Unstructured Supplementary Service information/data (USSD), Short Message Service (SMS), Multimedia Messaging Service (MMS), Dual-Tone Multi-Frequency Signaling (DTMF), and/or Subscriber Identity Module Dialer (SIM dialer). The virtual assistant client computing entity 102 can also download changes, add-ons, and updates, for instance, to its firmware, software (e.g., including executable instructions, applications, program modules), and operating system.

According to one embodiment, the virtual assistant client computing entity 102 may include location determining aspects, devices, modules, functionalities, and/or similar words used herein interchangeably. For example, the virtual assistant client computing entity 102 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including low Earth orbit (LEO) satellite systems, Department of Defense (DOD) satellite systems, the European Union Galileo positioning systems, the Chinese Compass navigation systems, Indian Regional Navigational satellite systems, and/or the like. Alternatively, the location information/data may be determined by triangulating the computing entity's position in connection with a variety of other systems, including cellular towers, Wi-Fi access points, and/or the like. Similarly, the virtual assistant client computing entity 102 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing entities (e.g., smartphones, laptops) and/or the like. For instance, such technologies may include iBeacons, Gimbal proximity beacons, BLE (Bluetooth Low Energy) transmitters, near field communication (NFC) transmitters, and/or the like. These indoor positioning aspects can be used in a variety of settings to determine the location of someone or something to within inches or centimeters.

The virtual assistant client computing entity 102 may also comprise a user interface device comprising one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, user interface, dashboard, webpage, and/or similar words used herein interchangeably executing on and/or accessible via the virtual assistant client computing entity 102 to cause display or audible presentation of information/data and for user interaction therewith via one or more user input interfaces. The user input interface can comprise any of a number of devices allowing the virtual assistant client computing entity 102 to receive data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the virtual assistant client computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the virtual assistant client computing entity 102 can collect information/data, user interaction/input, and/or the like.

The virtual assistant client computing entity 102 can also include volatile storage or volatile memory 322 and/or non-volatile storage or non-volatile memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the virtual assistant client computing entity 102. Again, as a specific example, the virtual assistant client computing entity 102 memory storage areas (encompassing one or both of the volatile memory 322 and/or non-volatile memory 324) may store the application thereon, which itself may encompass one or more artificial intelligence and/or machine-learning algorithms.

In one embodiment, the proactive query server computing entity 106 may further include or be in communication with volatile media (also referred to as volatile storage, memory, memory storage, memory circuitry and/or similar terms used herein interchangeably). In one embodiment, the volatile storage or memory may also include one or more volatile storage or memory media as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 305. Thus, the databases, database instances, database management system entities, data, applications, programs, program modules, scripts, source code, object code, byte code, compiled code, interpreted code, machine code, executable instructions, and/or the like may be used to control certain aspects of the operation of the virtual assistant client computing entity 102 with the assistance of the processing element 305 and operating system.

As indicated, in one embodiment, the proactive query server computing entity 106 may also include one or more network interfaces 320 for communicating with various computing entities, such as by communicating data, content, information, and/or similar terms used herein interchangeably that can be transmitted, received, operated on, processed, displayed, stored, and/or the like. For instance, the proactive query server computing entity 106 may communicate with computing entities or communication interfaces of other computing entities, the virtual assistant client computing entities 102, and/or the like. As indicated, in one embodiment, the proactive query server computing entity 106 may also include one or more network interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the proactive query server computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1x (1xRTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, NFC protocols, Wibree, Bluetooth protocols, USB protocols, and/or any other wireless protocol. The proactive query server computing entity 106 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), Hypertext Markup Language (HTML), and/or the like.

The virtual assistant client computing entity 102 may be embodied by a virtual assistant device comprising virtual assistant services capable of performing tasks for a user based on, for example, user input and information accessible over a network from third party databases. Virtual assistant services may include playing music, retrieving information, sending messages, making telephone calls, setting reminders, performing internet searches, or any other actions in response to a user request. In some embodiments, the virtual assistant device may connect to a network and communicate with virtual assistant client computing entities 102 and/or IoT devices to share data or execute control commands (e.g., turn of lights in living room, set coffee maker to 6 am, etc.). It will be understood that the examples of virtual assistant devices described herein are merely exemplary, and the system of the present disclosure may be implemented using any suitable hardware and/or software.

Exemplary System Operation

Reference will now be made to FIGS. 4-11. FIG. 4 is a flowchart 400 illustrating operations and processes related to the generation and presentation of a proactive audiovisual query in order to obtain query response data and performance of one or more responsive actions based on the query response data. FIGS. 5-11 each describe one or more aspects of implementation of one or more steps/operations of FIG. 4.

Retrieving User Experience Data

In some embodiments, a user may be associated with a user profile accessible to the proactive query server computing entity 106 via the virtual assistant client computing entity 102. For example, a user or someone on behalf of a user can create a user profile or update a user profile via a user interface of a virtual assistant software application provided by the proactive query server computing entity 106 for storage and use by the proactive query server computing entity 106.

In an example embodiment, the virtual assistant software application enables the virtual assistant client computing entity 102 to retrieve user experience data (Block 401 of FIG. 4). Such user experience data may include the user's bibliographic data, such as the user's name, gender, birthdate, age, and/or the like. Further, such information may include record numbers for the user's EMR, EHR, and/or personal health record (PHR). In one embodiment, such medical data can be semi-automatically or automatically retrieved. To retrieve this medical data, the proactive query server computing entity 106 may send a request for user medical information to one or more EMR, HER, and/or PHR systems using one or more application programming interface (API) calls. In response, the one or more EMR, EHR, and/or PHR systems may retrieve the user medical information from a corresponding medical records database and return the user medical information to the proactive query server computing entity 106 via the network. In some embodiments, the proactive query server computing entity 106 may request access to the EMR, HER, and/or PHR systems' APIs beforehand to ensure that the API requests from the proactive query server computing entity 106 are valid and authorized.

EMR, EHR, and/or PHR medical record data includes a collection of electronically stored information about a user's lifetime health status and health care corresponding to the user's medical history, surgeries, medication and allergies, symptoms, immunization status, laboratory test results, radiology images, vital signs, personal statistics like age and weight, primary care physician, specialist medical providers, health insurance information, health insurance authorizations (e.g., authorizations for durable medical equipment and/or outpatient surgery), medical claims, prescriptions, conditions, diagnoses, schedules, treatments, illnesses, concerns, payment information, family history, and/or the like. The EMR, EHR, and PHR systems may combine data from a number of health care services and providers, such as clinical care facilities, laboratories, radiology providers, and pharmacies.

User experience data can further include medication data from one or more multiple sources such as the user by inputting data regarding medications the user is taking to the virtual assistant software application and accessible by the proactive query server computing entity 106. Such medications may be prescribed by a medical professional or primary care physician or may include non-prescription medications such as over-the-counter drugs, vitamins, and/or herbal products that the user is taking.

Another source for medication data can include the medical professional or primary care physician providing updated prescription data to the proactive query server computing entity 106 through the virtual assistant software application provided by the proactive query server computing entity 106. In another example embodiment, the proactive query server computing entity 106 can obtain prescription data electronically, by email, by fax, by voice, or by any electronic transmissions through the virtual assistant software application provided by the proactive query server computing entity 106. Additionally, the medical professional or primary care physician can provide precautionary information such as specific side effects or adverse effects to watch for, and/or under what circumstances to contact the medical professional. In another example embodiment, the user using the virtual assistant software application may scan a barcode of the medication which retrieves medication data including a digitized image showing what the prescribed drug should look like. Once the proactive query server computing entity 106 obtains the medication data, the proactive query server computing entity 106 can reconcile and consolidate the list of medication data.

In some embodiments, the medication data may include drug identification information, dosage information, specific side effects, possible adverse side effects when taken in a certain manner or in combination with other medication, likelihood of an onset of other symptoms and diseases, user historical prescription information (e.g., refills, etc.), date and time information, identification information regarding the pharmacy, the user, and the prescribing medical profession, and other data. FIG. 5 illustrates a conceptual data model of a drug prescription profile for user profile A comprising user experience data. The drug prescription profile conceptual model of FIG. 5 includes a list of user experience events. Each user experience event identified as D1, D2, and D3 comprises user experience data related to one or more drug use events and/or one or more drug prescription events.

User experience data may further comprise environmental data and user tracking data. Environmental data may include all data that can be measured or captured in an environment and/or indicative of the context of the environment, such as a level of illumination, a level and spectrum of background noises, an activation state of an IoT device within the environment (e.g., TV, audio streaming device, heating state from connected thermostat, motion from third party home automation systems, power sensing level from whole-home power sensors or individual plug socket power sensing devices), and/or a user's proximity to an object or device. Home appliances and IoT devices such as a refrigerator, television, electric lamp, and the like are equipped with sensors (e.g., pyroelectric infrared sensors, motion sensors, etc.) to detect conditions of the home appliances such as opening/closing of the refrigerator and on/off of the tv and electric lamp and are equipped with functions to transmit the detected conditions in response to a request from the virtual assistant client computing entity 102 connected with such home appliances and IoT devices via a home network.

In some embodiments, environmental data may indicate a presence of a user within a proximity to a home appliance, IoT device, or the virtual assistant client computing entity 102. For example, a user proximity indicator for the user profile may be computed using at least a history of recorded physical closeness of the user to the virtual assistant client computing entity 102. The user proximity indicator may include any response recorded by a sensor of the virtual assistant client computing entity 102 that may be indicative of a user being within the area of the virtual assistant client computing entity 102. Alternatively, the user proximity indicator may include a series of responses from the sensor of the virtual assistant client computing entity 102 that no user is detected within the area of the virtual assistant client computing entity 102.

The virtual assistant client computing entity 102 collects and transmits the user proximity data and environmental data to the proactive query server computing entity 106 so that the proactive query server computing entity 106 may identify a query opportunity moment. For example, the virtual assistant client computing entity 102 can determine that the user proximity indicator has exceeded a proximity threshold and in response, the proactive query server computing entity 106 can detect the query opportunity moment based on the user proximity indicator.

The user experience data can define one or more user experience events for the user profile which represent an action associated with a user profile and/or an observation associated with the user profile. For example, any of the IoT devices or the virtual assistant client computing entity 102 can detect user-initiated actions or observations over time. Such events are recorded by the proactive query server computing entity 106 to determine a user's activity pattern in order to preemptively trigger presentation of the proactive audiovisual query.

Retrieving Subject Matter Domain Data

Returning to FIG. 4, the proactive query server computing entity 106 is configured to retrieve subject matter domain data (Block 402 of FIG. 4). In some embodiments, the proactive query server computing entity 106 is configured to retrieve subject matter domain data associated with one or more user experience events, wherein the subject matter domain data defines one or more probabilistic event effects for the one or more user experience events. For example, given a user experience event of taking Drug A, the probabilistic event effects may include side effects A1-A10.

In some embodiments, the proactive query server computing entity 106 is configured to identify one or more terms from the user experience event. In the example provided, the term of interest is "Drug A." The proactive query server computing entity 106 can then search EMR, EHR, PHR systems and/or medical knowledge bases (e.g., medical journals, world drug reports, etc.) to identify Drug A and other terms of interest (e.g., known side effects) associated with Drug A. An example search result may be that Drug A causes severe nausea, abdominal pain, and dry skin. In some embodiments, the terms are processed and analyzed until a predetermined threshold is reached, indicating that enough data has been collected to develop a valid probabilistic event set, to be applied to the generation of the proactive audiovisual query that the proactive query server computing entity 106 generates.

The proactive query server computing entity 106 is then configured to build a probabilistic data model from the terms and/or relationship information found in the one or more user experience events and the probabilistic event effects. These probabilistic data models are stored to the subject matter domain data knowledge base as subject matter domain data. In another example embodiment, the subject matter domain data knowledge base may store training data collected from previously acquired user medical records and acquired user experience event and probabilistic event set relationship truths. For example, the training data and associated user experience event and probabilistic event set relationship truths are correlated with terms and relationships search results to train the probabilistic data model. In some embodiments, the proactive query server computing entity 106 is then configured to use the subject matter domain data comprising the probabilistic data model for mining one or more probabilistic event effects for the one or more user experience events.

Determining Optimal Query Items

Within the present disclosure, the proactive query server computing entity 106 may define one or more optimal query item computation processes. An optimal query item computation process implements optimal query item determination strategies that are unique to each user and based on user experience data. In an example embodiment, an optimal query item computation process calculates a per-item priority score and temporal cost, identifies time-eligible query combinations, and for each time-eligible query combination, determines a combined priority score to determine the optimal query items. The optimal query items selected to be provided as part of a proactive audiovisual query to the user during a query opportunity moment.

Returning to FIG. 4, after the proactive query server computing entity 106 retrieves the user experience data and the subject matter domain data, the process continues with block 403 where the proactive query server computing entity 106 determines optimal query items. An exemplary process for optimal query item determination is presented in FIG. 6. The exemplary process for optimal query item determination 600 begins with determining desired query items. (Block 601). A query item may include one or more terms or keywords (e.g., drug brand name, drug generic name, etc.) related to a specific drug. In some embodiments the query items are associated with at least one of one or more probabilistic event effects. For example, the one or more probabilistic event effects may include one or more potential side effects of taking Drugs 1, 2, or 3 (or any combination of Drugs 1, 2, 3) of drug prescription profile for user profile A 500 of FIG. 5. In some embodiments, the one or more probabilistic event effects comprise one or more probabilistic drug side effects, wherein the probabilistic drug side effects are based on subject matter domain data. The subject matter domain data defines one or more probabilistic event effects for one or more user experience events.

In some embodiments, the probabilistic event effect is determined using a probabilistic data model having trained probabilities for drug-side-effect relationships based on medical expert systems, drug side effect data of a plurality of users, medical knowledge bases, patient reported knowledge bases, and/or user medical records. In other words, the probabilistic data model may provide probabilistic reasoning for the existence, a chance of existence, or lack of a potential side effect for a particular user based at least in part on the user's medical record and user experience data. FIG. 7 provides an example output table 700 from the optimal query item computation process. The output table 700 of FIG. 7 includes a column for a side effect ID 701 for a probabilistic drug side effect and a column for drug correlation 702, linking a probabilistic drug side effect and a drug. In other words, a probabilistic drug side effect can be correlated to a drug. As shown in the output table, side effect ID S1 is connected to drug D1, side effect ID S2 is connected to drugs D1 and D2, side effect ID S3 is connected to drugs D1 and D3, side effect ID S4 is connected to drugs D1, D2, and D3. In some embodiments, when two or more drugs are listed, it is a combination of the two or more drugs that are connected to the side effect.

As discussed herein, a one or more desired query items or questions is associated with one or more probabilistic event effects. Once the one or more probabilistic event effects comprising one or more probabilistic drug side effects are determined, the proactive query server computing entity 106 may access the one or more EMRs, EHRs, PRO-CTCAE, user profile, and/or medical knowledge bases to gather information about the one or more probabilistic drug side effects. For example, the one or more EMRs, EHRs, PRO-CTCAE, user profile, and/or medical knowledge bases may include standard questions or scripts associated with each of the one or more probabilistic drug side effects. The proactive query server computing entity 106 may initially use a standard question as an initial desired query item. In some embodiments, the proactive query server computing entity 106 may adapt or transform the initial desired query item to a different type such as multiple choice instead of an open question type. The proactive query server computing entity 106 may adapt or transform the initial desired query item based on user experience data, environmental data, or the user's recorded activity pattern.

Continuing with the process for determining optimal query items as presented in FIG. 6, the proactive query server computing entity 106 is configured to, for each desired query item, determine a per-item priority score and a temporal cost (Block 602). The per-item priority score is determined based on the estimated significance (side effect severity score) of a probabilistic drug side effect to a condition of a user profile. For example, the significance or impact of an allergy drug-side-effect-related query item on a particular user may be scored according to the severity of the user's reaction. For example, the user may have an allergic reaction to penicillin with a side effect severity score of 0.3, but an allergic reaction to copper with a side effect severity score of 0.8. FIG. 7 shows an example output table 700 including a side effect severity score 703 column and a side effect priority score 704 column. According to the table, D1 has a side effect severity score 0.5 and a side effect priority score 0.2. A combination of D1 and D2 has a side effect severity score 0.9 and a side effect priority score 0.7.

The temporal cost for each desired query item may be calculated based on the lexical semantic structure of the desired query item, desired query item type (e.g., open vs closed), desired query item method (e.g., written, audio-only, audio-visual, etc.), or historical query-and-answer data. For example, it takes nearly 20 seconds to out query item Q1. Put another way, the virtual assistant service Alexa™ may take 20 seconds to audibly emit "Do you feel nauseous?" and receive a corresponding response to the audible emission. In another example, the virtual assistant service Siri® may take 10 seconds to visually display "Do you feel nauseous?" on the display of a mobile device and receive a corresponding response to the displayed prompt. FIG. 8 provides an example output table 800 from the optimal query item computation process and in particular the query item ID 801 and side effect ID 802 for the desired query item and calculations for the temporal cost 803. According to the output table 800 of FIG. 8, query item ID Q1 has a temporal cost 20 seconds, query item Q2 has a temporal cost of 40 seconds, query item Q3 has a temporal cost of 10 seconds, and query item Q4 has a temporal cost of 30 seconds.

Once the per-item priority score and the temporal cost is determined for each desired query item, the proactive query server computing entity 106 is configured to identify time-eligible query combinations (Block 603 of FIG. 6). Each time-eligible query combination of the time-eligible query combinations is associated with a related subset of one or more desired query items whose combined temporal cost falls below the estimated time capacity for a particular optimal temporal range for presenting the proactive audio-visual query. The estimated time capacity is associated with an optimal temporal range, where the optimal temporal range is optimal period of time that is suitable for presenting the proactive audiovisual query. For example, given a combination of query items Q1 and Q2, the estimated time capacity is estimated to take two minutes and is within the optimal temporal range of two minutes and twenty seconds.

At Block 604 of FIG. 6, the proactive query server computing entity 106 is configured to, for each time-eligible query combination, determine a combined priority score. The combined priority score is determined is based on each per-item priority score for a desired query item of the one or more desired query items that is in the related subset for the time-eligible query combination. FIG. 9 provides an example output table 900 from the optimal query item computation process and in particular the combined temporal cost 902 for the query item combination 901 and the combined priority score 903 for the query item combination 901. According to the output table 900 of FIG. 9, query item combination Q1+Q3 has a combined temporal cost of 30 seconds and a combined priority score 0.6. The query item combination Q4 had a combined temporal cost of 30 seconds and a combined priority score 0.8. As shown in the example output table 900 of FIG. 9, the proactive query server computing entity 106 computes the combined temporal cost for query item combination Q1+Q3 as the sum of the temporal cost for Q1 and the temporal cost for Q3 found in FIG. 8. The proactive query server computing entity 106 is further configured to compute the combined priority score for query item combination Q1+Q3 as the sum of the side effect priority score for Q1 and the side effect priority score for Q3 found in FIG. 8.

In Block 605 of FIG. 6, the proactive query server computing entity 106 is configured to determine the optimal query items. Determining the optimal query items is based on each combined priority score for a time-eligible query combination of the plurality of time-eligible query combinations. In some embodiments, determining the optimal query items is based on a combination of potential query items whose combined temporal cost falls below the estimated time capacity optimal temporal range for a proactive audiovisual query during the query opportunity moment and whose combined priority score is higher than the combined priority score for other combinations of potential query items. For example, in accordance with the output table 900 of FIG. 9, among the two depicted time-eligible query item combinations, the time-eligible query item combination that consists of Q4 may be selected because the noted time-eligible query item combination has a higher combined priority score 903 than the other time-eligible query item combination, i.e., the time-eligible query item combination consisting of Q1 and Q3.

Generating the Proactive Audiovisual Query

Returning to FIG. 4, the proactive query server computing entity 106 is configured to generate the proactive audiovisual query (Block 404). The proactive audiovisual query is generated in accordance with the one or more optimal query items. For example, in FIG. 9 query item combination Q1+Q3 may be selected by the proactive query server computing entity 106 to be provided as part of a proactive audiovisual query to the user during a query opportunity moment. In this case, the proactive query server computing entity 106 compares the combined temporal cost of each query item combination in FIG. 9. As shown in the output table, both query item combinations, Q1+Q3 and Q4 have a combined temporal cost of 30 seconds. Query item combination Q4 has a higher combined priority score 0.8 than query item combination Q1+Q3 which has a combined priority score of 0.6.

The proactive query server computing entity 106 is then configured to detect a query opportunity moment (Block 405). Detecting the query opportunity comprises i) during the optimal temporal range, determining a user proximity indicator for the user profile based on environmental data recorded by the virtual assistant software application; and ii) detecting the query opportunity moment based on the user proximity indicator.

In some embodiments, in order to determine an optimal temporal range (e.g., time of day, day of the week, etc.) to present the proactive audiovisual query, the recorded activity pattern for a user profile is analyzed. User activity state (e.g., reading, listening to music, watching tv, eating, sleeping, working, exercising, etc.), at a given point in time (e.g., points in time) is assigned an activity factor, where the activity factor represents a user engagement level with the activity. For example, a user is highly engaged watching a movie, the user is not available to respond to the proactive audiovisual query. However, a user exhibits low engagement emptying the dishwasher, the user is likely to respond to the proactive audiovisual query.

During an optimal period of time that is suitable for presenting the proactive audiovisual query (i.e., the optimal temporal range), the proactive query server computing entity 106 is configured to determine a user proximity indicator for the primary user profile based on environmental data recorded by the virtual assistant software application. The user proximity indicator, determined based on the environmental data from the virtual assistant software application, provides an indication of the user's position within the environment.

In some embodiments, the virtual assistant software application runs on a smart phone, IoT device, virtual assistant device, or the like. Such devices are connected via a home network. The virtual assistant software application may request environmental data from the connected devices and may analyze the environmental data to determine the user's position within the environment. The environmental data may include a history of recorded physical closeness of the user to one or more of the connected devices such as the virtual assistant client computing entity 102. In some embodiments, the virtual assistant client computing entity 102 may include a sensor configured to detect a proximity of the user to the virtual assistant client computing entity 102. The proximity sensor provides the user proximity indicator when the user is within a threshold distance from the virtual assistant client computing entity 102. The proactive query server computing entity 106 may then detect the query opportunity moment based on the user proximity indicator. In other words, the proactive audiovisual query may be presented based at least in part on presence detection of the user as indicated by the user proximity indicator. This ensures that the user is present when the proactive audiovisual query is presented to the user; in such cases, the presentation of the proactive audiovisual query should be relatively contemporaneous with detection/identification of the user to ensure presence of the user. Accordingly, the proactive query server computing entity 106 is configured to cause presentation of the proactive audiovisual query during the query opportunity moment (Block 406 of FIG. 4).

In this way, when the user is near the virtual assistant client computing entity 102, the proactive audiovisual query may be customized to the user (based on detection of the presence of the user and/or based on detection of the presence of the user's personal device being used by the user, the user's profile, recorded activity information about the user, other information about the user, and/or the like). In an example embodiment, the proactive audiovisual query may be presented by the virtual assistant software application implemented on the virtual assistant client computing entity 102 during the query opportunity moment. In some embodiments, the proactive audiovisual query may be presented via audio and/or video where the and the proactive audiovisual query may be transmitted to the audio and/or video of a TV or mobile client computing device, wearable device or other virtual assistant computing entity. Alternatively, or additionally, the proactive audiovisual query may be presented via e-mail message, text message, chat message, short message service ("SMS") message, multi-media messaging service ("MMS") message, videomail message, voicemail message, and/or other messaging communications. In some embodiments, presenting the proactive audiovisual query may be based at least in part on user preferences and recorded activity from the user profile, monitored reactions of the user to previously presented proactive audiovisual queries, and/or the like.

In Block 407, the proactive query server computing entity 106 is configured to receive query response data. The query response data from the user or the user using a client computing device may include audio data, visual data, or a combination of both audio data and visual data. In some embodiments, the query response data to the proactive audiovisual query is received by the virtual assistant client computing entity 102, subsequent to which the virtual assistant client computing entity 102 transmits the information to the proactive query server computing entity 106. In some embodiments, the virtual assistant software application implemented on the virtual assistant client computing entity 102 may be configured to determine whether the query response data constitutes an appropriate response (e.g., an audible combination of words). If the response is not an appropriate response, the virtual assistant client computing entity 102 may optionally present the proactive audiovisual query again or move on to the next optimal query item of the proactive audiovisual query.

In Block 408 of FIG. 4, the proactive query server computing entity 106 may be configured to perform responsive actions based on the query response data. In some embodiments, the one or more response action comprises the proactive query server computing entity 106 transmitting the query response data to the one or more EMR, EHR, PHR systems or the user's primary care physician. In some embodiments, the proactive query server computing entity 106 transmits the query response data to a research platform for academic and/or industrial research. In some embodiments, the proactive query server computing entity 106 transmits the query response data to one or more pharmaceutical companies, providers, insurers, or prescription server companies such as a drug formulary. In some embodiments, the proactive query server computing entity 106 transmits the query response data to other medical software services for updating a prescribed medicinal treatment regimen (e.g., update medication dispenser to increase drug dosage). The proactive query server computing entity 106 may also transmit the query response data to one or more internal or external databases or drug interaction databases. Consistent with health organizational policies, Health Insurance Portability and Accountability Act (HIPAA) guidelines, or any other privacy or security laws, such query response data will anonymize sensitive, personal data, and/or utilize generic references. In some embodiments, the proactive query server computing entity 106 may generate one or more alerts or notifications. The one or more alerts or notifications (e.g., provider notifications) may then transmitted to the medical professional or primary care physician when a side effect or drug interaction is identified. In some embodiments, the proactive query server computing entity 106 may alert or provide a notification such as a provider notification to the medical professional or primary care physician when a side effect or drug interaction is identified. The proactive query server computing entity 106 may also alert the user, such that the user may contact their primary care physician and confirm proper medicinal treatment regimen instructions. In some embodiments, performing the one or more responsive actions comprises performing one or more load balancing operations for a medical provider institution and/or a medical provider server, e.g., for a hospital institution and/or a hospital server.

In another example embodiment, the proactive query server computing entity 106 may analyze the query response data to determine desired query items as discussed with reference to the process for optimal query item determination 600 of FIG. 6. The proactive query server computing entity 106 may generate one or more inferred event effects based on the query response data and update the one or more probabilistic event effects based on the query response data. In other words, the proactive query server computing entity 106 may refine the originally posed proactive audiovisual query based on the query response data. Thus, the query response data may be used to refine an intent of the proactive audiovisual query, clarify the proactive audiovisual query, and potentially improve one or more values of the side effect severity score, side effect priority score, temporal cost, or drug correlation data.

Inferring Drug Side Effects

In some embodiments, the proactive query server computing entity 106 is configured to infer the presence of drug side effects from a database comprising user-specific drug information. Information about the user may be collected by the proactive query server computing entity 106. The information may be applied to train a probabilistic data model for determining likelihood of a side effect developing in a user based on query response data to the proactive audiovisual query and/or user experience data. For example, Statins drug class used to lower cholesterol has a known side effect of muscle cramps. Therefore, if the user is observed to have recently exercised, it can be inferred that the user may experience muscle pain as a side effect.

As discussed herein, the user profile stores information about the user, including biographic, demographic, and various other information categories, such as, but not limited to, medical history, current and past medications and allergies, immunizations, vital signs, personal statistics such as age and weight, and the like. The user profile may further include the user's recorded activity pattern. This information is securely stored in a database of the proactive query server computing entity 106 wherein each user profile is uniquely identified.

In some embodiments, the probabilistic model may be used to predict drug side effects based on past observations and current user experience data. The probabilistic model may further be used to synthesize the learnings from the past observations and/or query response data to proactive audiovisual queries. In this case, the proactive query server computing entity 106 is configured to collect user experience data prior to presentation of the proactive audiovisual query or application of a drug. For example, the proactive query server computing entity 106 may collect user experience data for two hours prior to application of a drug. In some embodiments, user experience data obtained closer to a time when the drug is taken by the user may be deemed to have more influence on the drug (e.g., trigger side effects, increase severity of side effects, etc.) than user experience data obtained farther from a time when the drug is taken.

In some embodiments, the proactive query server computing entity 106 may collect other user information such as the user's voice characteristics (e.g., tone, rate of speech, etc.), facial characteristics (e.g., dark circles under eyes, unsteadiness, etc.), purchase history, physical activity level, etc., to predict potential drug side effects. For example, the proactive query server computing entity 106 may retrieve a facial image of the user from the user's mobile device and may compare the facial image to a collection of predefined facial expressions or facial characteristics to predict one or more side effects.

In some embodiments, the proactive query server computing entity 106 may analyze the query response data to proactive audiovisual queries to predict one or more side effects. For example, the query response data from a proactive audiovisual query may indicate that the user may have a fever because the user reported feeling warm. Over the course of the day, the query response data to a second proactive audiovisual query may indicate that the user is no longer feeling warm. The proactive query server computing entity 106 may continuously track the user's reported temperature over a period of time and identify a pattern of user behavior and response to subsequent proactive audiovisual queries. Based on the pattern of user response to the subsequent proactive audiovisual queries, the proactive query server computing entity 106 may be able to determine a probability of the user developing or having a drug side effect.

Augmented Reality (AR) Drug Discovery

In some embodiments, the proactive query server computing entity 106 may provide AR drug discovery operations using an AR-based drug discovery application executable on a client computing device. The operations may include generating a user-specific drug side effects overlay associated with a drug onto an image of the drug that is being captured by a client computing device. For example, as shown in FIG. 10A, the user may activate a camera of the client computing device to capture a barcode, label portion or unique identifier on a medication bottle 1000. Each barcode, label portion or unique identifier is linked to information about the drug captured. In an example embodiment, the AR-based drug discovery application retrieves the drug information and generates user-specific drug side effects information 1050 to be displayed on the client computing device as shown in FIG. 10B. The user-specific drug side effects information is based on the user profile. In some embodiments, the generated user-specific drug side effects information may include a listing of general side effects associated with the drug and another listing of the general side effects associated with the drug with a calculated relevance percentage in relation to the user. The relevance percentage may be provided to the user as a way to quantify the relevance or likelihood the user will develop the drug side effect based on the user profile. For example, the user profile takes into account the observation that the user is a male and therefore the drug side effect of vaginal itching or discharge has a zero-percentage likelihood of occurring. In another example, the user profile takes into account the gastrointestinal complications in a patient's history and thus increases the depicted likelihood that the particular patient may experience gastrointestinal side effects of a particular drug. In yet another example embodiment, the AR-based drug discovery application may highlight (e.g., increased font size, underline, etc.) the drug side effects relevant to the user in a graphical overlay above the original side effect text on the medicine bottle.

Distributed Transmission of User Response Data

As part of analyzing user responses to proactive audiovisual queries, the proactive query server computing entity 106 may transmit all or part of the noted user response data to various predefined recipient institutions. For example, the proactive query server computing entity 106 may transmit information about side effects experienced by a user to computing devices associated with medical providers of the user. As another example, the proactive query server computing entity 106 may transmit information about side effects experienced by a user to computing devices associated with insurance institutions and/or payer institutions associated with the user. As yet another example, the proactive query server computing entity 106 may transmit information about side effects experienced by a user to computing devices associated with pharmacy institutions and/or with drug formulary institutions. As a further example, the proactive query server computing entity 106 may transmit information about side effects experienced by a user to an EMR server in order to update the EMR of the user in accordance with the recorded side effects of the user. As another example, the proactive query server computing entity 106 may transmit information about side effects experienced by a user to a computing device associated with a research institution.

In some embodiments, the proactive query server computing entity 106 may transmit user response data to a centralized cross-user data aggregation server. The centralized cross-user data aggregation server may in turn be configured to process user response data obtained from many proactive query server computing entities associated with many users in order to generate population-wide response data, and then provide the population-wide data to at least one of medical provider computing devices, pharmacy computing devices, drug formulary institution computing devices, payer institution computing devices, health insurance institution computing devices, research institution computing devices, university computing devices, and/or the like. In some embodiments, the proactive query server computing entity 106 may transmit user response data to the centralized cross-user data aggregation server in an anonymized form and/or using an encrypted data transmission channel (e.g., an end-to-end-encrypted data transmission channel) between the proactive query server computing entity 106 and the centralized cross-user data aggregation server.

In some embodiments, the proactive query server computing entity 106 stores the user response data in a cloud storage environment associated with a user. In some embodiments, the proactive query server computing entity 106 processes the user response data along with one or more alert generation guidelines to detect alert-related events based on the user response data. In some of the noted embodiments, subsequent to detecting an alert-related event, the proactive query server computing entity 106 generates medical alerts corresponding to the alert-related event to at least one of medical provider computing devices, pharmacy computing devices, drug formulary institution computing devices, payer institution computing devices, health insurance institution computing devices, research institution computing devices, university computing devices, and/or the like. In some of the noted embodiments, subsequent to detecting an alert-related event, the proactive query server computing entity 106 schedules one or more medical appointments and/or generates one or more automated drug prescriptions to address the alert-related event. In some of the noted embodiments, subsequent to detecting an alert-related event, the proactive query server computing entity 106 contacts an emergency medical service provider server to notify a corresponding emergency medical service provider of the alert-related event.

CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

For example, the foregoing description provides various examples of utilizing systems and computer-implemented methods for generating queries related to determining drug side effects. However, it should be understood that various embodiments of the systems and computer-implemented methods discussed herein may be utilized for monitoring user's adherence with a prescribed medicinal therapy regimen, assessing a user's exercise level, emotional state, and/or the like.

The invention claimed is:

1. A computer-implemented method for facilitating presentation of a proactive audiovisual query using a virtual assistant software application, the computer-implemented method comprising:
    retrieving, by a processor, user experience data associated with a user profile for the virtual assistant software application, wherein the user experience data define one or more user experience events for the user profile;
    retrieving, by the processor, subject matter domain data associated with the one or more user experience events, wherein the subject matter domain data define one or more probabilistic event effects for the one or more user experience events;
    determining, by the processor and based at least in part on the user experience data and the subject matter domain data, one or more optimal query items, wherein (a) the one or more optimal query items are associated with at least one of the one or more probabilistic event effects, and (b) determining the one or more optimal query items comprises:
        (1) determining one or more desired query items, wherein the one or more desired query items are associated with the one or more probabilistic event effects,
        (2) for each desired query item of the one or more desired query items, determining a per-item priority score for each desired query item and a temporal cost for each desired query item,
        (3) identifying a plurality of time-eligible query combinations, wherein each time-eligible query combination of the plurality of time-eligible query combinations is associated with a related subset of the one or more desired query items whose combined temporal cost falls below the estimated time capacity,
        (4) for the each time-eligible query combination of the plurality of time-eligible query combinations, determining a combined priority score based at least in part on the per-item priority score for the each desired query item of the one or more desired query items that is in the related subset for the each time-eligible query combination, and
        (5) determining the one or more optimal query items based at least in part on the combined priority score for each time-eligible query combination of the plurality of time-eligible query combinations;
    generating, by the processor, the proactive audiovisual query in accordance with the one or more optimal query items;
    detecting, by the processor, a query opportunity moment; and
    causing, by the processor, the virtual assistant software application to present the proactive audiovisual query during the query opportunity moment.

2. The computer-implemented method of claim 1, wherein the one or more user experience events comprise one or more drug assignment events.

3. The computer-implemented method of claim 1, wherein the one or more probabilistic event effects comprise one or more probabilistic drug side effects.

4. The computer-implemented method of claim 1, further comprising:
    determining, based at least in part on a recorded activity pattern for the user profile, an optimal temporal range for the proactive audiovisual query, wherein the optimal temporal range is associated with an estimated time capacity.

5. The computer-implemented method of claim 4, wherein detecting the query opportunity moment comprises:
    determining the query opportunity moment based at least in part on the optimal temporal range.

6. The computer-implemented method of claim 1, wherein detecting the query opportunity moment further comprises:
    during the optimal temporal range, determining a user proximity indicator for the user profile based at least in part on environmental data recorded by the virtual assistant software application; and
    detecting the query opportunity moment based at least in part on the user proximity indicator.

7. The computer-implemented method of claim 1, further comprising:
    receiving query response data from the virtual assistant software application; and
    performing one or more responsive actions based at least in part on the query response data.

8. The computer-implemented method of claim 7, wherein performing the one or more responsive actions comprises generating one or more provider notifications based at least in part on the query response data.

9. The computer-implemented method of claim 8, wherein performing the one or more responsive actions comprises:
    generating one or more inferred event effects based at least in part on the query response data; and updating the one or more probabilistic event effects based at least in part on the query response data.

10. An apparatus for facilitating presentation of a proactive audiovisual query using a virtual assistant software application, the apparatus comprising at least one processor and at least one memory including program code, the at least one memory and the program code configured to, with the processor, cause the apparatus to at least:
    retrieve user experience data associated with a user profile for the virtual assistant software application, wherein the user experience data define one or more user experience events for the user profile;
    retrieve subject matter domain data associated with the one or more user experience events, wherein the subject matter domain data define one or more probabilistic event effects for the one or more user experience events;
    determine, based at least in part on the user experience data and the subject matter domain data, one or more optimal query items, wherein (a) the one or more optimal query items are associated with at least one of the one or more probabilistic event effects, and (b) determining the one or more optimal query items comprises:
- (1) determining one or more desired query items, wherein the one or more desired query items are associated with the one or more probabilistic event effects,
- (2) for each desired query item of the one or more desired query items, determining a per-item priority score for each desired query item and a temporal cost for each desired query item,
- (3) identifying a plurality of time-eligible query combinations, wherein each time-eligible query combination of the plurality of time-eligible query combinations is associated with a related subset of the one or more desired query items whose combined temporal cost falls below the estimated time capacity,
- (4) for the each time-eligible query combination of the plurality of time-eligible query combinations, determining a combined priority score based at least in part on the per-item priority score for the each desired query item of the one or more desired query items that is in the related subset for the each time-eligible query combination, and
- (5) determining the one or more optimal query items based at least in part on the combined priority score for each time-eligible query combination of the plurality of time-eligible query combinations;

generate the proactive audiovisual query in accordance with the one or more optimal query items;

detect a query opportunity moment; and cause the virtual assistant software application to present the proactive audiovisual query during the query opportunity moment.

11. The apparatus of claim 10, wherein the one or more user experience events comprise one or more drug assignment events.

12. The apparatus of claim 10, wherein the one or more probabilistic event effects comprise one or more probabilistic drug side effects.

13. The apparatus of claim 10, further comprising:
determining, based at least in part on a recorded activity pattern for the user profile, an optimal temporal range for the proactive audiovisual query, wherein the optimal temporal range is associated with an estimated time capacity.

14. A computer program product for facilitating presentation of a proactive audiovisual query using a virtual assistant software application, the computer program product comprising at least one non-transitory computer-readable storage medium having computer-readable program code portions stored therein, the computer-readable program code portions configured to:

retrieve user experience data associated with a user profile for the virtual assistant software application, wherein the user experience data define one or more user experience events for the user profile;

retrieve subject matter domain data associated with the one or more user experience events, wherein the subject matter domain data define one or more probabilistic event effects for the one or more user experience events;

determine, based at least in part on the user experience data and the subject matter domain data, one or more optimal query items, wherein (a) the one or more optimal query items are associated with at least one of the one or more probabilistic event effects, and (b) determining the one or more optimal query items comprises:
- (1) determining one or more desired query items, wherein the one or more desired query items are associated with the one or more probabilistic event effects,
- (2) for each desired query item of the one or more desired query items, determining a per-item priority score for each desired query item and a temporal cost for each desired query item,
- (3) identifying a plurality of time-eligible query combinations, wherein each time-eligible query combination of the plurality of time-eligible query combinations is associated with a related subset of the one or more desired query items whose combined temporal cost falls below the estimated time capacity,
- (4) for the each time-eligible query combination of the plurality of time-eligible query combinations, determining a combined priority score based at least in part on the per-item priority score for the each desired query item of the one or more desired query items that is in the related subset for the each time-eligible query combination, and
- (5) determining the one or more optimal query items based at least in part on the combined priority score for each time-eligible query combination of the plurality of time-eligible query combinations;

generate the proactive audiovisual query in accordance with the one or more optimal query items;

detect a query opportunity moment; and cause the virtual assistant software application to present the proactive audiovisual query during the query opportunity moment.

15. The computer program product of claim 14, wherein the one or more user experience events comprise one or more drug assignment events.

16. The computer program product of claim 14, wherein the one or more probabilistic event effects comprise one or more probabilistic drug side effects.

17. The computer program product of claim 14, further comprising:
determining, based at least in part on a recorded activity pattern for the user profile, an optimal temporal range for the proactive audiovisual query, wherein the optimal temporal range is associated with an estimated time capacity.

* * * * *